United States Patent [19]
Seddon et al.

[11] Patent Number: 6,024,731
[45] Date of Patent: Feb. 15, 2000

[54] WOUND DRAINAGE SYSTEM

[75] Inventors: Peter Seddon, Cheltenham; David Foster, Oxford, both of United Kingdom

[73] Assignee: Summit Medical Ltd., Gloucester, United Kingdom

[21] Appl. No.: 09/051,683

[22] PCT Filed: Oct. 17, 1996

[86] PCT No.: PCT/GB96/02549

§ 371 Date: Jun. 15, 1998

§ 102(e) Date: Jun. 15, 1998

[87] PCT Pub. No.: WO97/14449

PCT Pub. Date: Apr. 24, 1997

[30] Foreign Application Priority Data

Oct. 18, 1995 [GB] United Kingdom .................... 9521397

[51] Int. Cl.⁷ .................................................. A61M 1/00
[52] U.S. Cl. ........................... 604/317; 604/320; 604/119
[58] Field of Search .................................. 604/27, 30, 33, 604/35, 118, 119, 140, 141, 317, 319, 320, 323, 324; 600/573, 578, 579

[56] References Cited

U.S. PATENT DOCUMENTS

| | | | |
|---|---|---|---|
| 3,624,821 | 11/1971 | Henderson | 604/320 |
| 3,833,000 | 9/1974 | Bridgman | 604/320 |
| 4,112,949 | 9/1978 | Rosenthal et al. | 604/319 |
| 4,372,336 | 2/1983 | Cornell et al. | 604/319 |
| 4,642,093 | 2/1987 | Harle | 604/54 |
| 4,675,011 | 6/1987 | Kurtz et al. | 604/320 |
| 4,930,997 | 6/1990 | Bennett | 604/319 |
| 5,073,172 | 12/1991 | Fell | 604/119 |
| 5,236,425 | 8/1993 | Kurtz et al. | 604/320 |

*Primary Examiner*—Corrine McDermott
*Assistant Examiner*—David J. Cho
*Attorney, Agent, or Firm*—Alix, Yale & Ristas, LLP

[57] ABSTRACT

A low vacuum wound drainage system comprising a high vacuum bottle having an on/off switch to allow/prevent release of the vacuum from the bottle, and a connector for connection of a wound drainage line such that a vacuum path is provided between the bottle and the wound drainage line when the on/off switch is in the on position. The wound drainage line is adapted to be detachably connected to the vacuum bottle via the connector to apply suction at a patient end of the line and includes a regulating valve incorporated in the detachable wound drainage line, the valve acting to continuously regulate the vacuum in the line, when the line is attached to the bottle, to provide a reduced vacuum at the patient end of the line. Also a wound drainage line including a regulating valve for use with a high vacuum bottle.

17 Claims, 7 Drawing Sheets

WOUND DRAINAGE SYSTEM

CROSS-REFERENCE TO RELATED APPLICATIONS

This is the national stage of International Application No. PCT/GB96/02549 filed Oct. 17, 1996.

BACKGROUND OF THE INVENTION

The present invention relates to wound drainage systems.

During surgery and afterwards, during recovery, it is often necessary to remove fluid and wound secretions from the site of the wound.

Although previously vacuum pumps were used, it is now conventional to use vacuum suction flasks.

The suction flask is evacuated to a high level of vacuum, normally around 600 to 700 mm Hg. A flexible tube is connected to the flask and the other end of the tube is connected to a perforated wound drainage tube. The wound drainage tube, in turn, is introduced into a hermetically sealed wound cavity. When the line from the flask is opened, the negative pressure prevailing in the flask acts in the wound cavity thus drawing off wound secretions down the line into the flask.

Once the flask is full or the vacuum is no longer sufficient to draw off fluid, the system may be safely disposed of.

Flasks as described above are well-known and such flasks are disclosed in, e.g. EP-A-288679 and Swiss Patents 596, 840 and 584,037. However, as stated above, these flasks are charged with a high vacuum, e.g. around 96 kPa (720 mm Hg) and substantially all of that vacuum acts on the patient.

In certain medical applications, however, such high vacuums cannot be applied to the patient. This is particularly the case in e.g. cranial or abdominal surgery where a much lower vacuum, in the region of 13.3 to 20 kPa (100 to 150 mm Hg) is needed at the patient end of the wound drainage line.

Systems have, therefore, been developed to reduce the vacuum from a high vacuum suction flask. One such system is disclosed in EP 0 616 815.

In this system, the vacuum in the flask is adjusted to the desired level by first attaching a pressure measuring device to the neck of the flask. A valve is arranged between the flask and an adjustment device. The measuring device and adjustment device control the opening of the valve until the desired pressure is reached. The adjustment device is then removed and the wound drainage line is attached to the now low vacuum suction flask.

This system, however, is cumbersome and inefficient. It is only used to adjust the vacuum before use. Normally, however, flasks are supplied in a ready-charged, high vacuum state, ready to be attached to the wound drainage line. It would therefore be desirable to provide a vacuum regulating system which can be attached to a standard high vacuum flask and which regulates the vacuum at the patient end during use if a low vacuum system is required.

WO 99/05319 discloses a wound drainage bottle which, in one embodiment, has a vacuum reducer to regulate vacuum levels in order to maintain a constant vacuum in the bottle throughout the entire filling process.

For reasons of economy and convenience, a maximum vacuum is desirable in the suction flask in order to enable the greatest amount of wound secretion to be sucked into the flask before another flask is needed. However, as discussed above, in systems where the vacuum in the flask acts directly on the wound, the suction level in the wound region is too high for some applications.

Also, it is now common practice to use disposable wound drainage systems and, therefore, the cost of manufacture should be kept as low as possible whilst maximizing the capacity of each flask.

One known way of stepping down the vacuum from the flask to the patient is to use clips on the flexible wound drainage tube to reduce its cross-section. The system disclosed in DE-B-2356480 uses a flexible tube clip which causes the cross-section of the wound drainage tube to be closed to a certain extent for regulation of the internal pressure of the vacuum container. With this system, however, it is not possible to ensure that outside the sharply constricted cross-section of the flexible tube, a constant negative pressure largely independent of the negative pressure prevailing in the container can be maintained.

The system disclosed in EP-B-0482029 aims to provide a flexible tube clip with a simple way of reducing the cross-section of a flexible tube in order to form a throttle restriction. When used in a tube connection between a vacuum suction flask and a wound drainage tube, this clip can act independently as a throttle valve.

This system and other known systems use a bellows-type arrangement, integrally formed in a cap attached to the suction flask.

In the bellows system, two pivotal arms are fastened to a bellows arranged on the outside of the cap such that when the bellows are contracted, the arms close together compressing the cross-section of the tube lying between them. When the tube clip is open, the same negative pressure prevails in the tube as in the flask. The same negative pressure is also formed in the bellows. This causes the bellows to contract thus closing the arms of the clip which compress the tube. The resulting reduced negative pressure consequently acts in the wound drainage tube. With the tube closed, the flow from the wound has the effect of raising the pressure in the suction tube and bellows. This allows the bellows and thus the tube to open slightly passing fluid into the flask and again reducing the vacuum. Thus, in operation, the bellows continually regulate and maintain a fairly constant tube opening.

Although this system performs well, effectively and accurately reducing the vacuum to the desired level it does have several disadvantages. In particular, the regulation system is formed as an integral unit with the vacuum flask. It is thus necessary to purchase the whole system for a low vacuum requirement rather than converting an already charged high vacuum bottle for low vacuum use if desired.

SUMMARY OF THE INVENTION

It is desirable, therefore, to provide a vacuum regulation system which can be used with existing high vacuum suction flasks to provide accurate continuous negative pressure regulation during use.

The regulation system should be suitable for converting existing, high vacuum flasks for low vacuum applications as required without requiring any modification to the currently used flasks. The flask can thus be used for either high or low vacuum applications.

The present invention thus provides a low vacuum wound drainage system comprising a high vacuum bottle having on/off means to allow/prevent release of the vacuum from the bottle, and connector means for connection of a wound drainage line such that a vacuum path is provided between the bottle and the wound drainage line when the on/off means is in the on position; the system further comprising a wound drainage line adapted to be detachably connected to the vacuum bottle via the connector means to apply suction at a patient end of the line; and wherein a regulating valve is incorporated in the detachable wound drainage line, said valve acting to continuously regulate the vacuum in the line, when the line is attached to the bottle, to provide a reduced vacuum at the patient end of the line; characterised in that said valve comprises a valve spool slidingly located within a valve body and held by a spring, and wherein said valve body includes a patient line port and a high vacuum port, the former being connected to a section of the wound drainage tube leading to the patient and the latter being connected to a section of the wound drainage tube leading to the high vacuum bottle; and wherein the spring rate and the cross-sectional area of the valve spool to control the is degree of vacuum reduction from the high vacuum source to the patent line, are selected such that the return force of the spring and the pressure in the patient line acting on the line side of the spool equal the external atmospheric pressure acting agaist the other side of the spool when the vacuum in the patient line is the required low vacuum.

Thus, the same high vacuum flask can be used for high vacuum applications by connecting a simple wound drainage tube, or can be used for low vacuum applications by connecting a wound drainage tube incorporating an in-line regulating valve. The flask may be of standard construction.

The valve comprises a valve spool slidingly located within a valve body and held by a spring. Such a system overcomes disadvantages of the prior art bellows arrangements.

With a bellows device, in order to prevent a high vacuum surge when the system is switched on, it is necessary to prime the device by initially compressing the bellows. This has proved to be awkward in practice since one hand is needed to squeeze the bellows while, at the same time, the other hand is needed to switch the on/off switch.

The bellows system is also relatively bulky and cumbersome.

Accordingly viewed from a second aspect the invention provides a low vacuum wound drainage system comprising a high vacuum bottle having an outlet port and connector means and a wound drainage line connected or adapted to be connected at one end to the outlet port of the bottle via the connector to apply suction to another, patient end; wherein a regulating valve continuously regulates the vacuum in the wound drainage line to provide a reduced vacuum at the patient end, and wherein the valve comprises a valve body and a valve spool slidingly located within the valve body, the spool being spring loaded and arranged for reciprocal movement so as to periodically open and close the valve to provide said continuous regulation in said line.

Such a system is easier to prime than a bellows system and is more compact.

The system can be primed by initially pushing the valve spool inwards, against the force of the spring, before switching the system on.

Whilst the valve body, the ports and the connecting parts of the wound drainage line may be encased in a housing, part of the valve spool may project out from the housing to allow the valve to be primed before use by pressing the projecting part. The preferred embodiment, however, incorporates a priming pin which engages the end of the valve spool, at one end. The other end extends out of the valve body so that it can be pushed in by the user. The pushing force is transmitted to the valve spool, pushing it in against the spring force.

The priming pin is preferably in the form of a key which engages in the end of the valve spool. The pin preferably passes through a slot in the valve housing. The pin and the slot preferably cooperate such that after insertion into the slot, the pin can be rotated to a locked position to hold the valve in its primed position. Before use, the pin is rotated back to its unlocked position and removed.

In the preferred embodiment, a high vacuum port is provided in the side of the valve body such that movement of the spool into the body, against the force of the spring, cuts off this port from the inside of the valve body, and hence cuts off the path from the high vacuum source to an outlet port on the patient line side of the valve.

The spring rate is preferably selected to control the degree of vacuum reduction from the high vacuum source to the patient line, such that the spring return force begins to act against the external atmospheric pressure acting on the opposite side of the spool when the vacuum in the patient line is at the desired level.

The valve is preferably provided in a flexible wound drainage line adapted to be attached to a standard precharged high Vacuum flask or bottle.

The vacuum is preferably reduced from the standard supplied high vacuum of 80 to 93 kPa (600 to 700 mm Hg) to a low vacuum of 13.3 to 26.6 kPa (100 to 200 mm Hg).

Since the in-line regulating valve of the present invention can be used with standard high-vacuum flasks which can, if desired, be converted for use in low vacuum applications, the present invention, according to a further aspect, provides a flexible wound drainage tube having a first section adapted to be connected to a high vacuum bottle and a second section to be applied to a wound, said first and second sections being interconnected via a regulating valve which acts to continuously provide a lower vacuum in the second section than that provided in the first section from the high vacuum bottle.

BRIEF DESCRIPTION OF THE DRAWINGS

A preferred embodiment of the present invention will now be described, by way of example only, with reference to the accompanying drawings.

DETAILED DESCRIPTION OF THE PREFERRED EMBODIMENTS

The system of the present invention controls the reduction of vacuum to the patient to a controlled level and maintains that level whilst ensuring the containing wound drainage vessel fills to its capacity.

Figure 1:
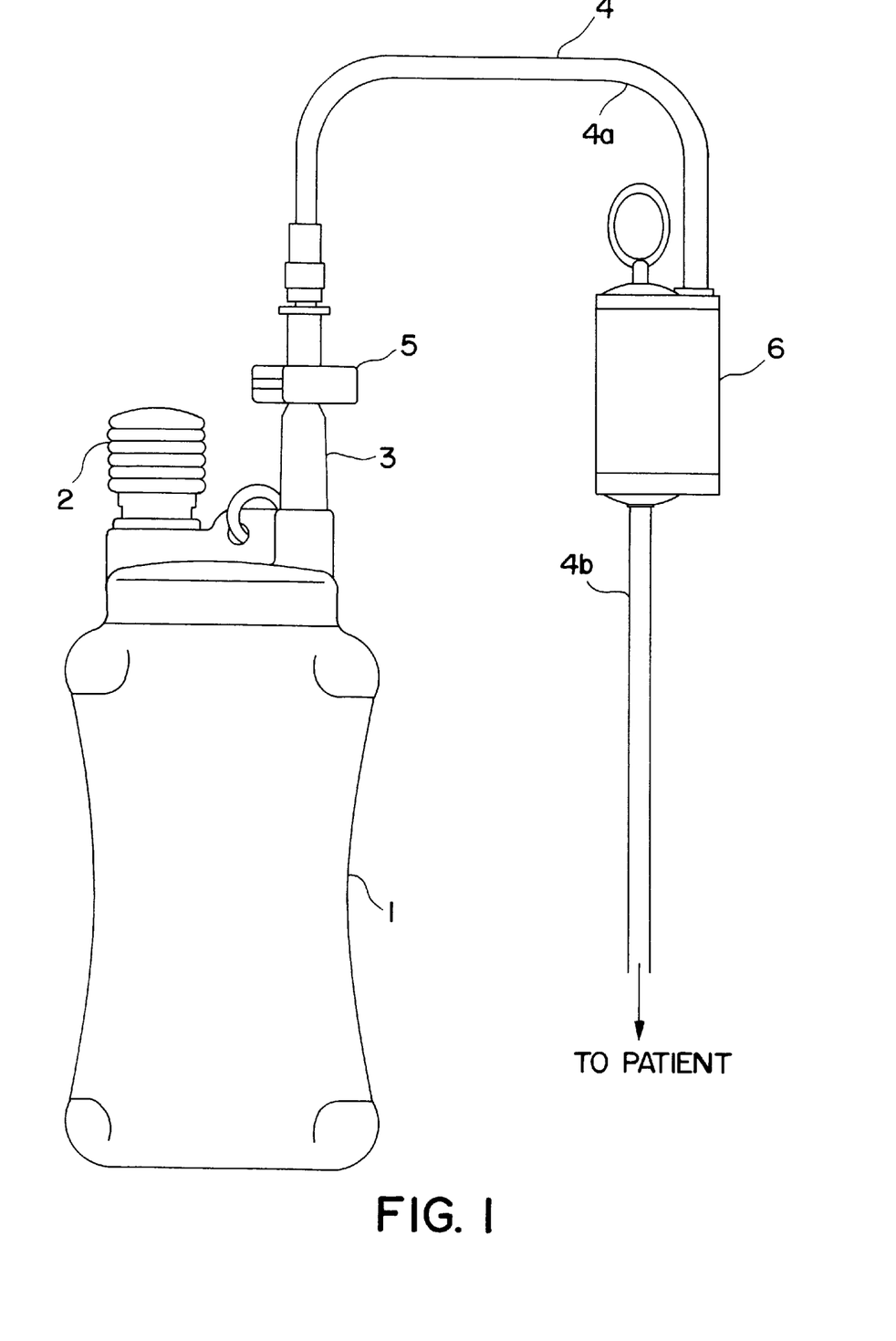
FIG. 1 shows a wound drainage system including an in-line valve in accordance with the present invention.

FIG. 1 shows a wound drainage suction apparatus incorporating an in-line regulating valve in accordance with the present invention.

The regulating device is positioned in the line between the patient and the collection vessel 1 which is also the high vacuum source. The vacuum source 1 is preferably a disposable, standard, pre-charged vacuum flask, supplied charged to a vacuum of 96 kPa (720 mm Hg).

There is a range of bottle sizes. A volume scale may be marked on the bottle to show the fill level and the bottle is at least partially transparent. Because disposable systems are preferred, the bottle will normally be made of plastic.

The standard bottles are provided with two openings. A bellows 2 is connected to one of these to provide an indication of the level of vacuum remaining in the flask 1. When the bellows 2 is at its maximum expansion, this indicates a minimum negative pressure or vacuum in the flask 1. A fully contracted bellows indicates a maximum vacuum.

A tube 3 is connected to the other opening in the flask 1. In use, this tube 3 will be connected to a flexible wound drainage tube 4. Before use, the tube 3 is closed by a clamp 5 which pinches the tube 3 to maintain the vacuum in the flask 1.

The bellows 2 and tube 3 may be enclosed in a plastic cap (not shown). The clamp 5 may also be enclosed in the cap and operated by an on/off switch on the outside of the cap. A port in the cap allows a wound drainage tube to be connected to the tube 3, in use.

Vacuum is applied to the patient via a flexible wound drainage tube 4 attached, at one end, to the vacuum flask 1 via the tube 3. The clamp 5 is opened causing the negative pressure in the flask 1 to exist in the drainage tube 4 and to be applied to the patient at the other end of the tube 4. This causes fluid and wound secretions to be drawn up the wound drainage tube, by suction, into the flask 1 which acts as the collection vessel. When the flask 1 is full, it is thrown away and a new charged vacuum flask is used.

As discussed above, it is often not appropriate to apply the source vacuum of 96 kPa (720 mm Hg) directly to the wound region. It is thus necessary to regulate the vacuum down to, say, 13.3 kPa (100 mm Hg) at the patient end of the drainage tube 4.

The aim of the present invention is to provide a constant low vacuum output at the patient end for as long as possible, to maximise efficiency and to allow the high vacuum source to be used for as long as possible. In an ideal situation, the vacuum at the patient end is constant at 13.3 kPa (100 mm Hg) while the high vacuum decreases from its initial value of say 96 kPa (720 mm Hg) to its finished, minimum value when it needs to be replaced.

The present invention provides this vacuum regulation by use of a valve 6 located in the wound drain age tube 4. The valve is attached at its two ports between two sections 4a, 4b of the flexible wound drainage tube 4 as shown in FIG. 1.

The construction and operation of the valve 6 will now be described in more detail, with reference to FIGS. 2 to 7.

Figure 2:
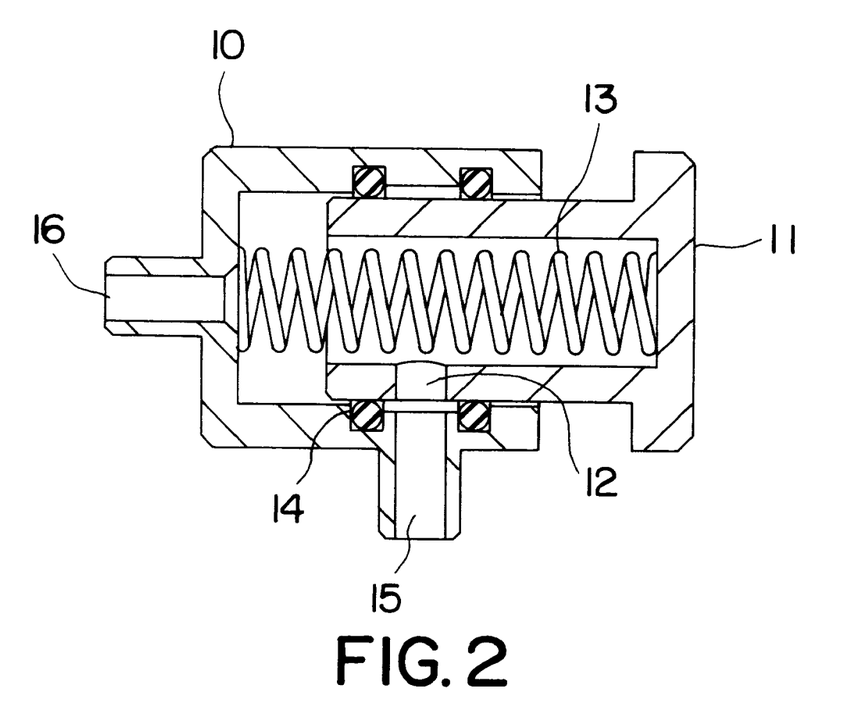
FIG. 2 shows the valve in the relaxed condition.
Figure 3:
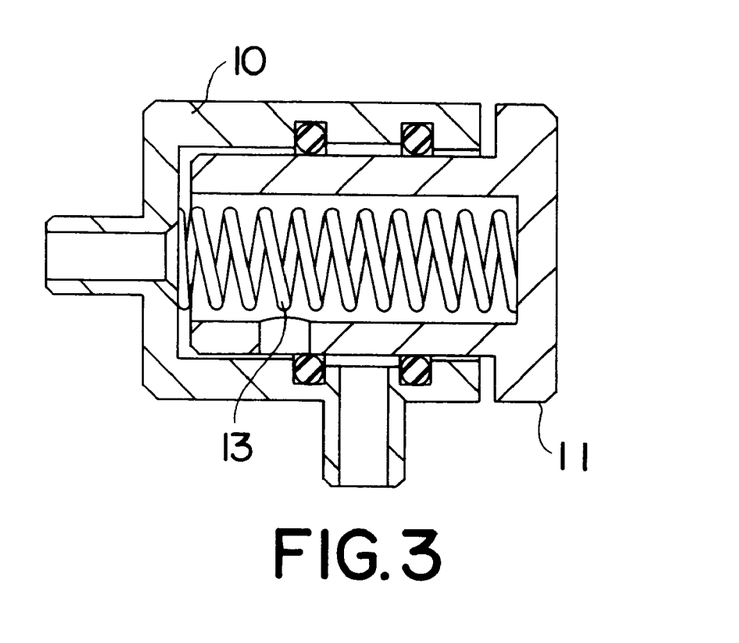
FIG. 3 shows the valve in a partially closed state.

The valve 6 essentially comprises a valve body 10, a spool 11, an orifice 12 in the spool 11, a spring 13, seals 14 and vacuum ports 15, 16 to the vacuum source 1 and the patient respectively. The valve parts are all preferably enclosed in a housing 18.

If the suction operation is commenced with the valve 6 in its relaxed position as shown in FIG. 2, a surge of high vacuum in the patient line may result. This is due to the initial long distance the spool 11 has to travel from the relaxed state of FIG. 2 to the shut-off state of FIG. 3.

In these circumstances, when the system is switched on, the patient would initially receive a dosage of vacuum above the desired rate. This could have an adverse effect on the patient, particularly in sensitive areas treated during abdominal or cranial surgery.

To overcome this problem, the valve should be primed for use by initially depressing the spool 11 and then opening the clamp 5 to release the high vacuum.

Figure 4:
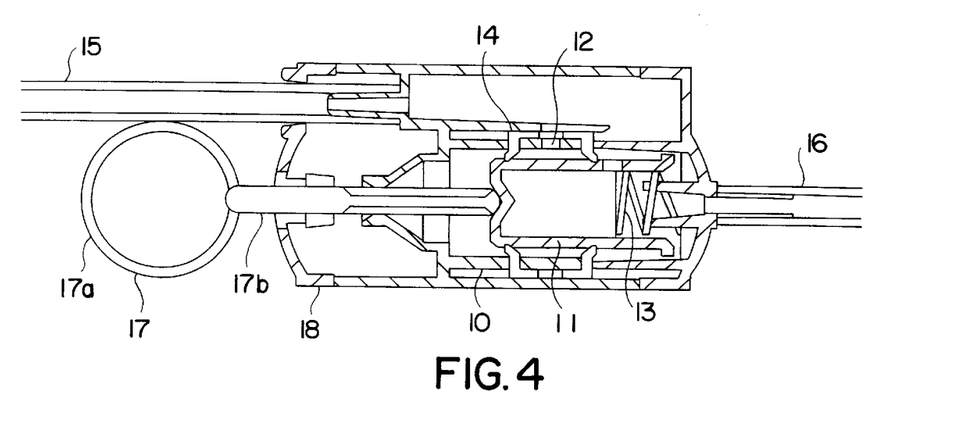
FIG. 4 shows a preferred embodiment of the valve in its primed position.

The preferred embodiment uses a priming pin 17 to prime the valve before use. The priming pin 17 is in the form of a key having a head 17a, adapted to be grasped by the user, and an elongate pin body 17b extending from the head 17a. The free end of the pin body 17b is shaped to engage in a notch or recess in the end of the valve spool 11.

Openings are provided in the valve body 10 and the valve housing 6, aligned with the notch or recess in the end of the spool 11. The openings correspond to the diameter of the priming pin 17. The pin 17 can thus be inserted through the openings and engage in the valve spool 11.

In one embodiment, the pin body 17b also has a pair of locking projections extending radially from the body 17b near the pin head 17a. The opening in the valve housing 18 is provided with corresponding recesses. When the priming pin 17 is inserted and pushed into the priming position, the locking projections engage in the recesses in the opening of the housing. If the pin is rotated, the projections move out of alignment with the recesses and lock the pin in place in its priming position.

This arrangement allows the valve to be sold and/or transported in the primed state. When the valve is to be used, the nurse or doctor only needs to unlock the pin by rotating it and then remove it after switching the device on.

Alternatively, the device may be sold with the valve in the unprimed, relaxed, state. In that case, the nurse needs to prime the valve before use by inserting the pin and pushing it to push the valve spool inwards against the spring force.

The regulating action of the valve 6 during wound drainage operation is now described.

After priming, the spring 13 will act to return the spool 11 to the position shown in FIG. 2, with the orifice 12 aligned with the high vacuum port 15. There is thus a complete path through the valve 6 between the high vacuum source 1 to the patient line via the valve ports 15, 16.

When the line to the high vacuum is opened, by opening the clamp 5, the vacuum level in the valve body 10 and the patient line will rise as the high vacuum draws/evacuates the valve and the patient line. Since the atmospheric pressure acting on the spool 11 is greater than the pressure on the patient side, the spool 11 is drawn into the valve body 10 against the force of the spring 13.

As the spool 11 continues to move, the orifice 12 passes over the seal 14 and is occluded by it thus cutting off the high vacuum. The point at which the orifice 12 passes over the seal 14 is the critical point at which the vacuum that has been allowed to develop in the patient line is the required low value, e.g. 13.3 kPa (100 mm Hg). This value is determined by the relationship between the vacuum acting on the end of the cross-sectional area (C.S.A.) of the spool 11 and the spring force of the compressed spring 13. Wound secretions/ fluid will then be drawn up the patient line by this lower regulated vacuum, into the valve body 10.

As the patient line fills as the wound is drained, the low vacuum level will start to fall. This lower vacuum will not be strong enough to hold the spool 11 against the return force of the spring 13. Thus, the spring 13 starts to return the spool 11 out of the valve body 10, allowing the orifice 12 to pass back over the seal 14 to align again with the high vacuum port 15.

The high vacuum will recharge the patient line until the spool 11 and its orifice 12 pass back over the seal 14 and also allows the material drawn up during the previous charge of the patient line to be passed into the collection vessel 1.

The cycle thus continues, performing constant regulation of the vacuum in the patient line, until the vessel 1 is full.

It is important that the low vacuum output at the patient end be as constant and smooth as possible over time. An important factor in providing a continuous smooth output is the surface resistance between the valve spool 11 and the seals 14. This resistance must be minimised as much as possible without losing the sealing effect.

In one embodiment, O-ring seals are provided on the valve body 10, shown in FIGS. 2 and 3, essentially corresponding to the two ends of the valve spool 11. It was found, however, that the surface contact, and hence the resistance, between the valve spool 11 and the seals 14 was too great and the low vacuum output did not provide a smooth, constant level trace over time, when measured.

Figure 6:
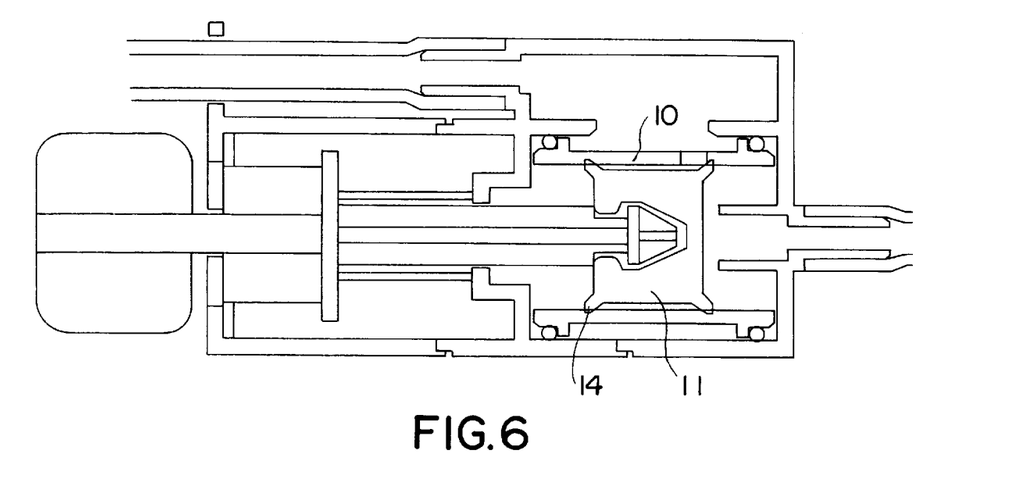
FIGS. 6 and 7 show alternative embodiments of a valve according to the present invention.

One arrangement considered, shown in FIG. 6, involved providing seals on the valve spool 11 itself, rather than on the valve body. To further reduce the surface contact, the O-ring seals were replaced by rubber feather-tip seals. The area of contact was thus reduced to a point at each seal and the resistance was also reduced.

Figure 7:
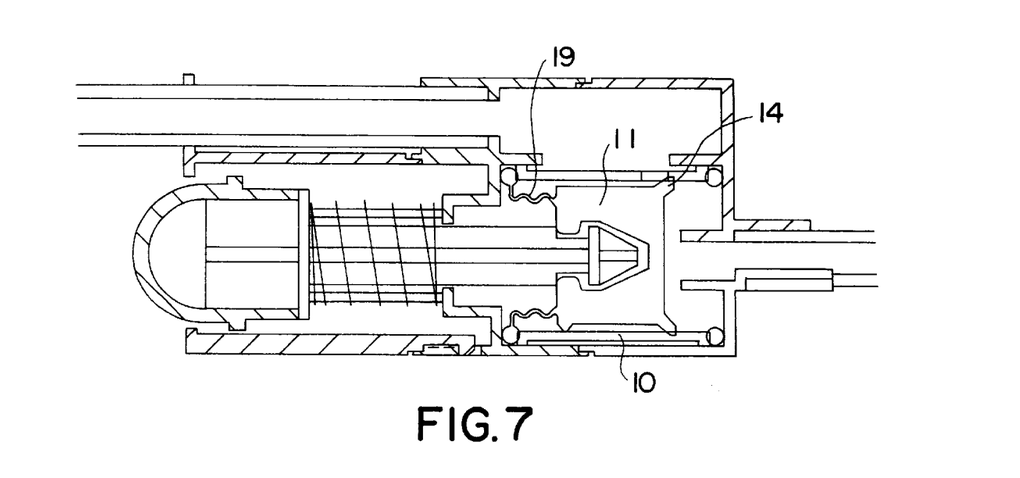
Figure 8A:
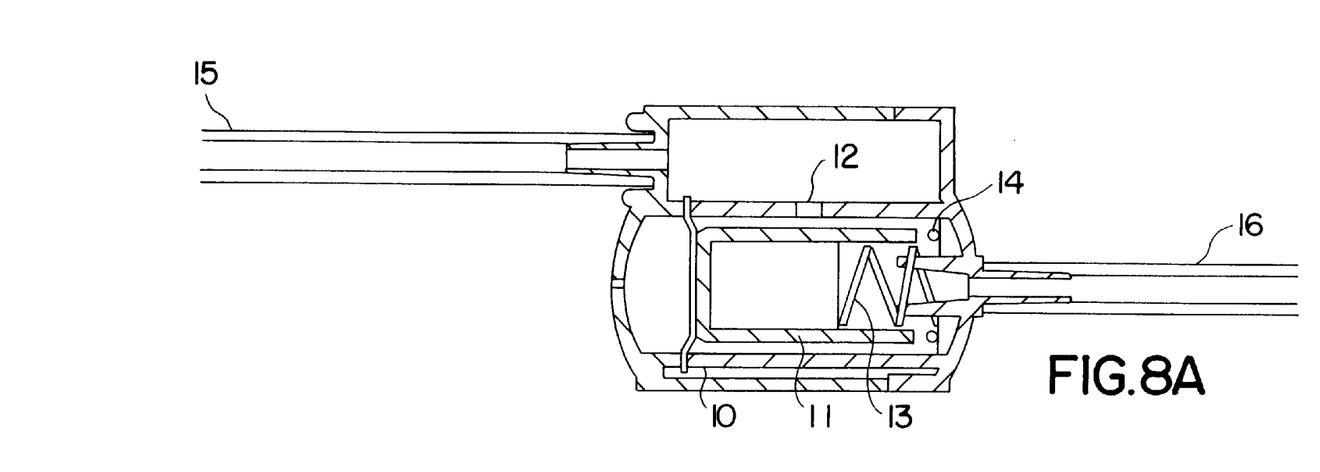
FIGS. 8A, 8B, 9A and 9B show the valve arrangements with and without vacuum for different sealing arrangements.
Figure 8B:
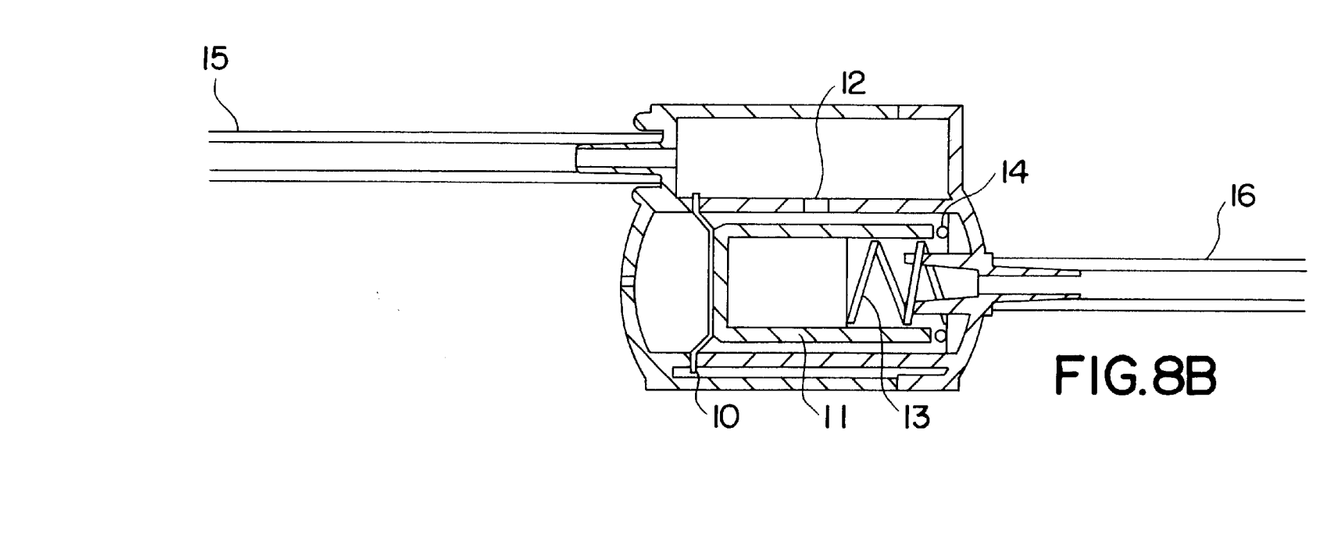
Figure 9A:
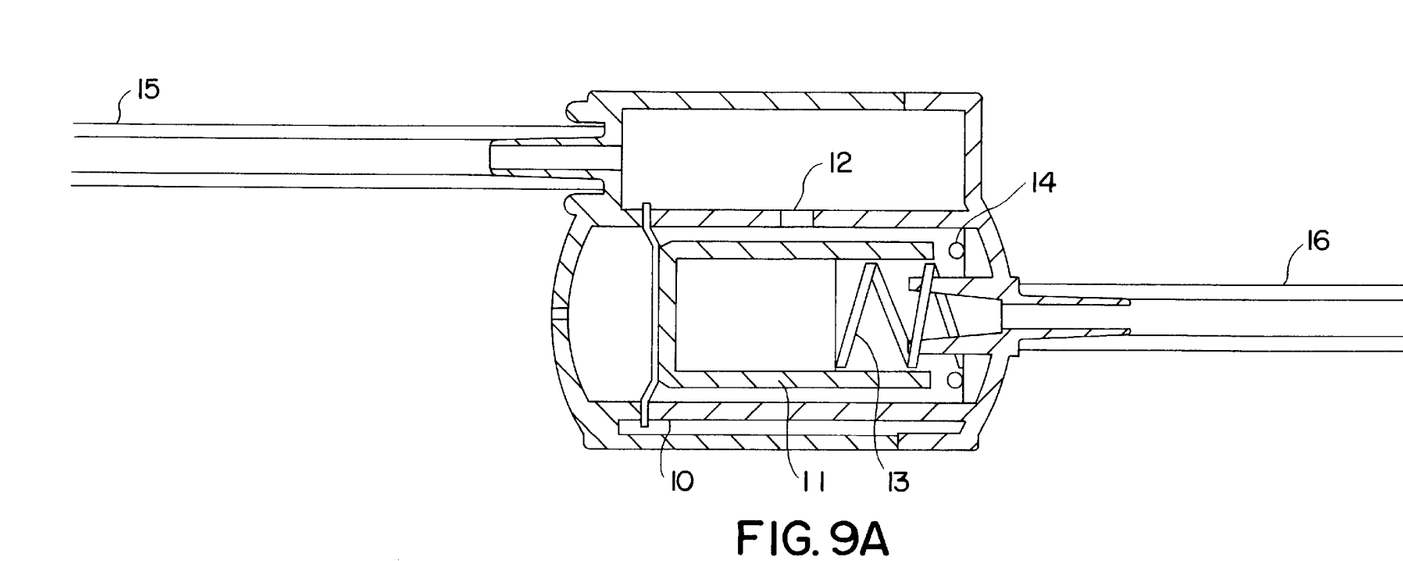
Figure 9B:
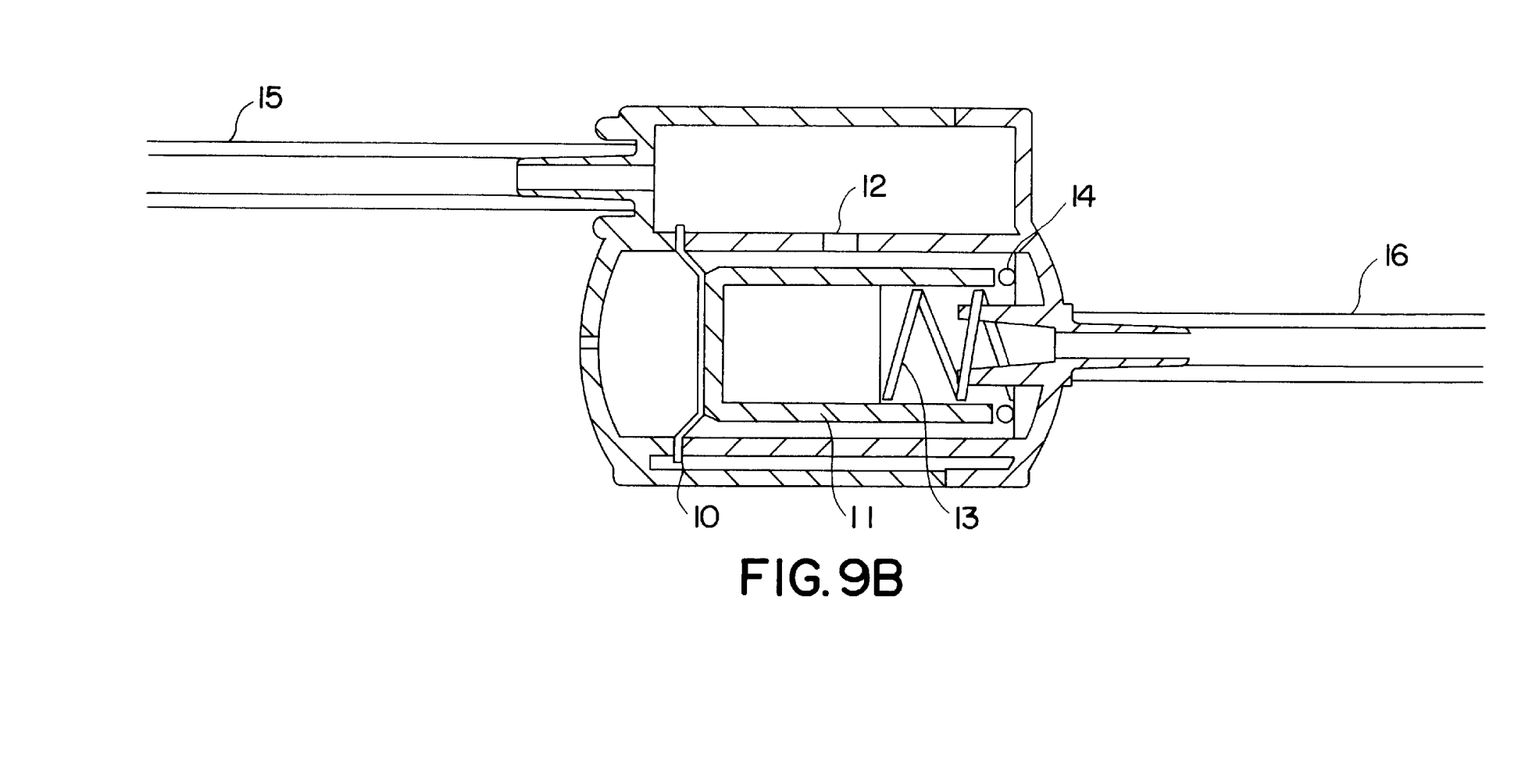

In a further embodiment shown in FIG. 7, one of the feather-tip seals was replaced by a flexible skirt 19 connected between the valve spool 11 and the valve body 10. The surface contact was thus reduced to a single point.

Although the use of seals on the valve spool 11 improved the smoothness of the low vacuum output over time, it was found that rather than a constant low vacuum being produced, the low vacuum output actually decreased over time, as the high vacuum in the flask decreased.

Figure 5:
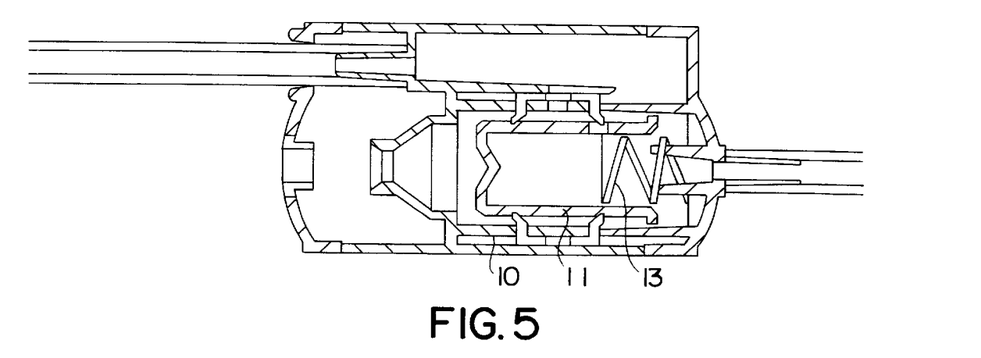
FIG. 5 shows the embodiments of FIG. 5 after removal of the priming pin.

The preferred embodiment, shown in FIGS. 4 and 5, thus uses seals on the valve body 10, corresponding to the ends of the sliding valve spool 11.

To reduce resistance, the preferred seals are a unique combination of an O-ring seal with a feather-tip seal. Such a seal ensures reliable sealing whilst having a small surface contact with the spool, at the point of the feather-tip. This arrangement has been found to produce a smooth, constant level low vacuum output over the drainage bottle's fill duration.

A further embodiment involves replacing one of the seals with a flexible skirt connected between the valve spool and the valve body.

The seals 14 and spool 11 may be coated to provide virtually no resistance between the parts to increase the accuracy of the system.

Whilst the main application for this device at present is for removal of wound secretions, another envisaged application is in autologous blood transfusion where a patient's blood is collected during an operation and subsequent recovery, then filtered and returned to the patient as a transfusion. This avoids problems in matching blood to a patient and also reduces the chances of infection from donated blood.

In autologous transfusion systems, blood cannot be collected under a high vacuum because this causes the red blood cells to break up.

The present low vacuum system could be used to collect the blood by providing the above-described valve in the line between a high vacuum reservoir and a collection vessel. The preferred level of vacuum in this application is around 9.3 to 14.7 kPa (70 to 110 mm Hg).

The present invention thus provides a neat, sophisticated, precise in-line vacuum regulating device for low vacuum medical use.

We claim:

1. A low vacuum wound drainage apparatus comprising a high vacuum bottle having on/off means to allow/prevent release of the vacuum from said bottle, and connector means for connection to a wound drainage line for establishing a vacuum path between said bottle and the wound drainage line when said on/off means is in the on position; said apparatus further comprising a detachable wound drainage line having a patient end and a second end and being adapted to be detachably connected to said vacuum bottle via said connector means to apply suction at said patient end of said wound drainage line; and a regulating valve incorporated in said detachable wound drainage line, said valve acting to continuously regulate the vacuum in said wound drainage line when said line is attached to said bottle to provide a reduced vacuum at said patient end of said wound drainage line; said valve comprising a valve spool slidingly located within a valve body and held by a spring, said valve body including a patient line port and a high vacuum port, said patient line port being connected to a section of said wound drainage tube which leads to said patient end and said high vacuum port being connected to a section of said wound drainage tube which leads to said high vacuum bottle; the spring rate and the cross-sectional area of said valve spool being selected to control the degree of vacuum reduction from the high vacuum of said bottle to said patient end of said wound drainage line, the return force of said spring and the pressure at said patient end of said wound drainage line acting on a first side of said spool and the external atmospheric pressure acting against a second opposite side of said spool, the forces acting on the opposite sides of said spool being equal when the vacuum in said wound drainage line at said patient end thereof is the required low vacuum.

2. The apparatus of claim 1, further comprising a priming pin adapted to force said valve spool into a primed position against the force of said spring.

3. The apparatus of claim 2, wherein said priming pin is in the form of a key which engages said first side of said valve spool.

4. The apparatus of claim 2, further comprising releasable locking means for holding said priming pin in its primed position.

5. The apparatus of claim 4, wherein said priming pin is in the form of a key which engages said first side of said valve spool.

6. The apparatus of claim 1, wherein said high vacuum port is located in the side of said valve body such that movement of said spool into said body, against the force of said spring cuts off said high vacuum port from the inside of said valve body, and hence interrupts the flow path from said high vacuum bottle to said patient line port in said valve body.

7. The apparatus of claim 1, wherein the spring rate of said spring is selected to control the degree of vacuum reduction from the high vacuum of said bottle to said patient end of said drainage line, such that the spring return force on said first side of said spool begins to act against the external atmospheric pressure acting on said second opposite side of said spool when the vacuum in the patient end of said wound drainage line is at the desired level.

8. The apparatus of claim 7, further comprising sealing means arranged between said valve spool and said valve body.

9. The apparatus of claim 8, further comprising a priming pin adapted to force said valve spool into a primed position against the force of said spring.

10. The apparatus of claim 9, further comprising releasable locking means to hold said priming pin in its primed position.

11. The apparatus of claim 10, wherein said priming pin is in the form of a key which engages said first side of said valve spool.

12. The apparatus of claim 1, further comprising sealing means arranged between said valve spool and said valve body.

13. The apparatus of claim 12, wherein said sealing means comprises seals of a combined O-ring and feather-tip configuration.

14. A low vacuum wound drainage apparatus comprising:

a high vacuum bottle having an outlet port and connector means;

a wound drainage line having a first end for connection to said outlet port of said bottle via said connector means whereby suction is applied to a second patient end of said drainage line; and a regulating valve for continuously regulating the vacuum in said wound drainage line to provide a reduced vacuum at said drainage line second end, said valve comprising a valve body, a valve spool arranged for sliding reciprocal movement within said valve body so as to periodically open and close said valve to provide said continuous regulation in said drainage line, a first side of said valve spool exposed to ambient atmospheric pressure, said spool being spring loaded by a spring, the spring rate of said spring selected to control the degree of vacuum reduction from said high vacuum bottle to said second patient end of said drainage line such that a spring return force on a second side of said spool begins to act against the external atmospheric pressure acting on the opposite side of said spool when the vacuum in the patient end of said wound drainage line is at the desired level, a side of said body having a high vacuum port such that movement of said spool into said body, against the force of said spring, cuts off said high vacuum port from the inside of said valve body, and hence interrupts the flow path from said high vacuum bottle to a second port in said valve body, said valve body second port being connected to said drainage line second end and a sealing means between said valve spool and said valve body.

15. The apparatus of claim 14, further comprising a primer for forcing said valve spool into a primed position against the force of said spring.

16. The apparatus of claim 15, further comprising locking means for holding said primer in its primed position.

17. A flexible wound drainage tube, comprising:

a first section adapted to be connected to a high vacuum bottle;

a second section to be applied to a wound; and a regulating valve interconnecting said first and second sections which acts to continuously provide a lower vacuum in the second section than that provided in the first section from the high vacuum bottle, said valve comprising:

a valve spool slidingly located within a valve body and held by a spring, said valve body including a patient line port and a high vacuum port, said patient line port being connected to said second section and said high vacuum port being connected to said first section, the spring rate and the cross-sectional area of said valve spool being selected to control the degree of vacuum reduction from the high vacuum of said bottle to said patient end of said wound drainage line, the return force of said spring and the pressure at said patient end of said wound drainage line acting on a first side of said spool and the external atmospheric pressure acting against a second opposite side of said spool, the forces acting on the opposite sides of said spool being equal when the vacuum in said wound drainage line at said patient end thereof is the required low vacuum.

* * * * *